(12) United States Patent
Singhatat

(10) Patent No.: US 7,357,803 B2
(45) Date of Patent: Apr. 15, 2008

(54) ROTATING RING LIGAMENT FIXATION

(75) Inventor: Wamis Singhatat, Malvern, PA (US)

(73) Assignee: Linvatec Corporation, Largo, FL (US)

( * ) Notice: Subject to any disclaimer, the term of this patent is extended or adjusted under 35 U.S.C. 154(b) by 614 days.

(21) Appl. No.: 10/700,241

(22) Filed: Nov. 3, 2003

(65) Prior Publication Data

US 2004/0176768 A1 Sep. 9, 2004

Related U.S. Application Data

(60) Provisional application No. 60/423,776, filed on Nov. 5, 2002.

(51) Int. Cl.
*A61B 17/56* (2006.01)

(52) U.S. Cl. .................... 606/62; 623/13.12

(58) Field of Classification Search ............. 606/56, 606/62, 64, 66, 72, 151; 623/13.11–13.14
See application file for complete search history.

(56) References Cited

U.S. PATENT DOCUMENTS

| | | | | |
|---|---|---|---|---|
| 4,246,660 A | * | 1/1981 | Wevers | 623/13.13 |
| 4,772,286 A | * | 9/1988 | Goble et al. | 623/13.14 |
| 4,834,752 A | * | 5/1989 | Van Kampen | 623/13.14 |
| RE34,293 E | * | 6/1993 | Goble et al. | 623/13.14 |
| 5,234,430 A | * | 8/1993 | Huebner | 606/60 |
| 5,282,802 A | * | 2/1994 | Mahony, III | 606/72 |
| 5,364,400 A | * | 11/1994 | Rego et al. | 606/72 |
| 5,632,748 A | * | 5/1997 | Beck et al. | 606/89 |
| 6,117,161 A | * | 9/2000 | Li et al. | 606/232 |
| 6,152,928 A | * | 11/2000 | Wenstrom, Jr. | 606/72 |
| 6,547,778 B1 | * | 4/2003 | Sklar et al. | 606/1 |
| 6,558,389 B2 | * | 5/2003 | Clark et al. | 606/72 |
| 2001/0007074 A1 | * | 7/2001 | Strobel et al. | 606/73 |
| 2002/0055780 A1 | * | 5/2002 | Sklar | 623/13.12 |

* cited by examiner

*Primary Examiner*—Corrine McDermott
*Assistant Examiner*—James L Swiger

(57) ABSTRACT

The present invention provides a graft retaining implant for retaining a graft in a bone tunnel formed in a bone. Instruments and methods are also provided for use with the graft retaining implant.

3 Claims, 4 Drawing Sheets

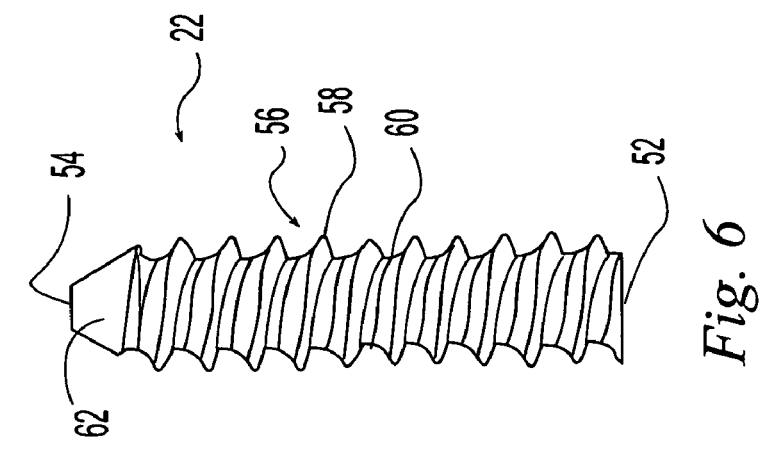
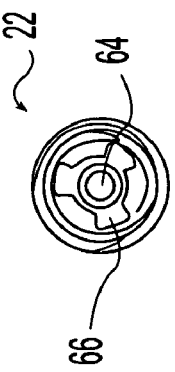
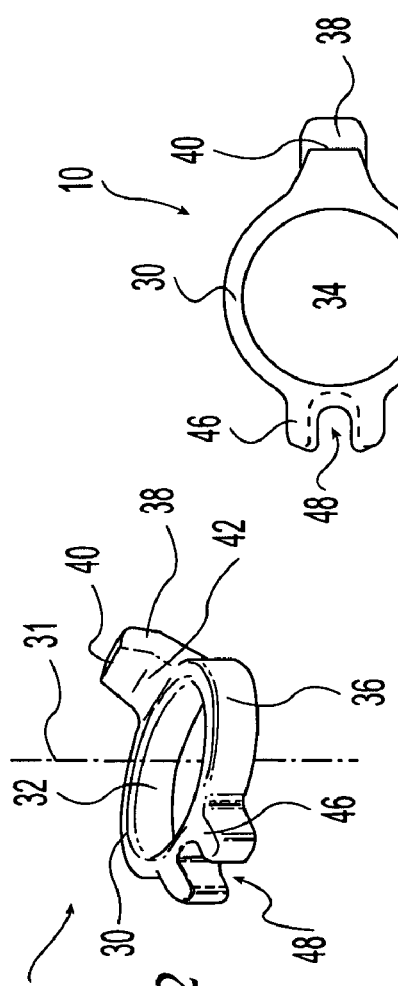
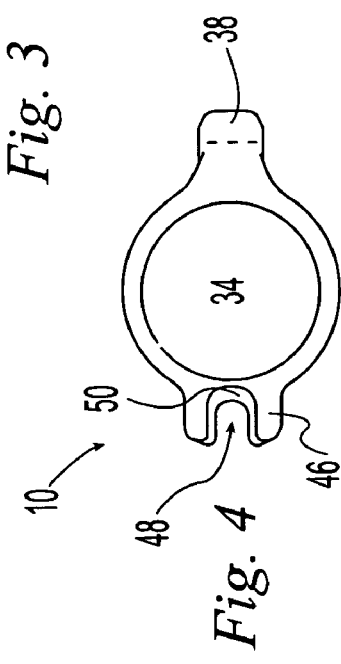
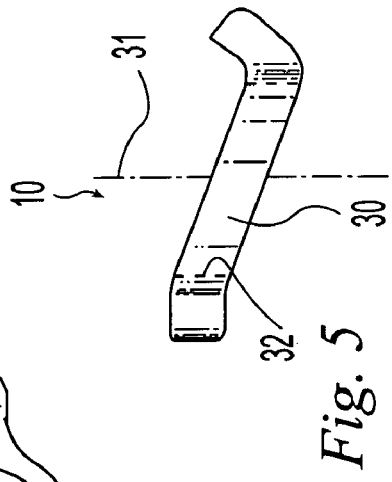
Fig. 2
Fig. 3
Fig. 4
Fig. 5
Fig. 6
Fig. 7

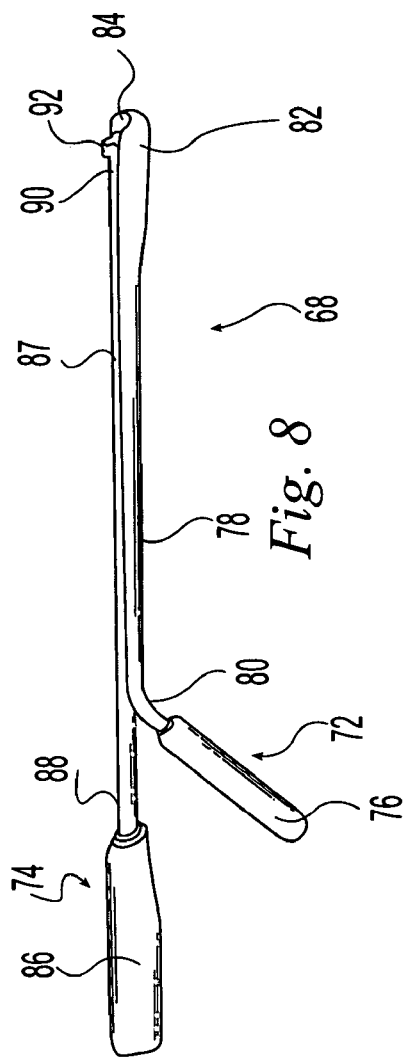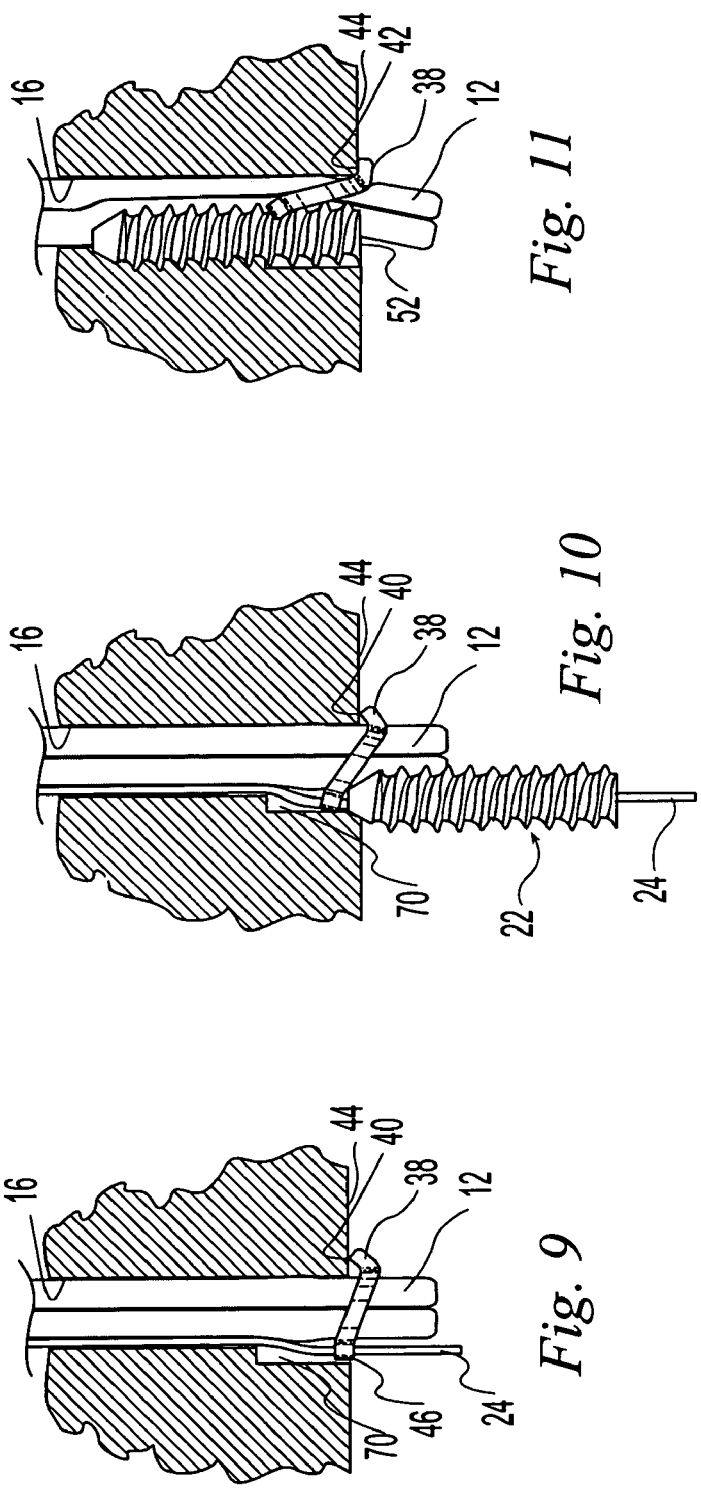

ROTATING RING LIGAMENT FIXATION

CROSS-REFERENCE TO RELATED APPLICATIONS

This application claims the benefit of U.S. Provisional Application No. 60/423,776, filed Nov. 5, 2002.

BACKGROUND

The invention relates to soft tissue repair and reconstruction. More particularly the invention relates to the fixation of a graft within a bone tunnel.

The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing within these bone tunnels a graft ligament. In many applications, such as in the knee joint, such procedures may be performed arthroscopically. The graft ligament may be an autograft, an allograft, a xenograft, and/or it may be totally artificial and synthetic. The most common types of graft ligaments include, for example, bone-tendon-bone grafts and soft tissue grafts such as semi-tendinosus and gracilis tendons. Both types are harvested by techniques well known to those skilled in the art. For example, repair of the anterior cruciate ligament (ACL) of the knee is often performed arthroscopically in a procedure which involves drilling a bone tunnel through the proximal tibia and into the distal femur. A variety of different types of graft ligaments may be secured in the bone tunnels in the femur and the tibia to replace the ACL.

Various fixation methods are used to secure the graft ligament within the femur and within the tibia. It is desirable that the fixation method be able to satisfactorily engage the bone in the wall of the bone tunnel or on the cortical bone surface. Consideration must be given to the fact that the bone may have only a thin layer of relatively hard cortical bone, such as in the anterior proximal surface and tibial plateau of the tibia. The bone may be otherwise relatively soft, cancellous bone. Depending upon the patient, the quality of the bone may vary considerably, particularly the cancellous bone. It would, therefore, be desirable to have a device capable of achieving fixation of the graft while eliminating the variability of fixation caused by the varying strength and density of cancellous bone.

Another consideration is that for biological graft fixation, that is, fixation resulting from tissue growing between the bone tunnel wall and the graft, some consideration should be given to facilitating such growth by enabling direct contact between the graft and the surrounding bone.

SUMMARY

The present invention provides a graft retaining implant for retaining a graft in a bone tunnel formed in a bone. Instruments and methods are also provided for use with the graft retaining implant.

In one aspect of the invention, a graft retaining system includes encircling means for at least partially encircling a portion of the graft and securing means for securing the graft and encircling means relative to the bone tunnel. The encircling means is movable from a first position in which the graft passes generally straight through the encircling means to a second position in which the graft is forced into a tortuous path through the encircling means such that the graft is gripped by the encircling means. The securing means secures the encircling means in the second position.

In another aspect of the invention, a graft retaining system includes a first member for gripping the graft, and a second member for securing the first member and the graft in the tunnel. The first member includes a portion for at least partially encircling the graft to grip the graft in belt buckle fashion when the first member is rotated relative to the graft.

In another aspect of the invention, a graft retaining system includes a ring including a cylindrical side wall having an axis. The cylindrical side wall is oriented parallel to a plane normal to the axis. The cylindrical wall has an inner surface defining a lumen for receiving the graft and an outer surface sized to fit within the bone tunnel. A bone engaging prong extends radially outwardly from the ring. A fixation tab extends radially outwardly from the ring, opposite the prong, for engaging an interference screw engageable with the fixation tab to secure the ring and graft relative to the tunnel.

In another aspect of the invention, a method for securing a graft in a bone tunnel includes providing encircling means for at least partially encircling a portion of the graft;

positioning the encircling means adjacent the bone tunnel in a first position such that it at least partially encircles a portion of the graft with the graft passing generally straight through the encircling means; and moving the encircling means from the first position to a second position in which the graft is forced into a tortuous path through the encircling means such that the graft is gripped by the encircling means.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 2 is a perspective view of the graft fixation device of FIG. 1.

FIG. 3 is a top plan view of the graft fixation device of FIG. 1.

FIG. 4 is a bottom plan view of the graft fixation device of FIG. 1.

FIG. 5 is a side elevation view of the graft fixation device of FIG. 1.

FIG. 6 is a side elevation view of an interference screw for use with the graft fixation device of FIG. 1.

FIG. 7 is an end view of the interference screw of FIG. 6.

FIG. 8 is a perspective view of an optional tunnel notching instrument used to prepare a bone tunnel to receive the graft fixation device of FIG. 1.

FIGS. 9-11 are partial side section views showing the implantation of the graft fixation device of FIG. 1.

DESCRIPTION OF THE ILLUSTRATED EMBODIMENTS

Figure 1:
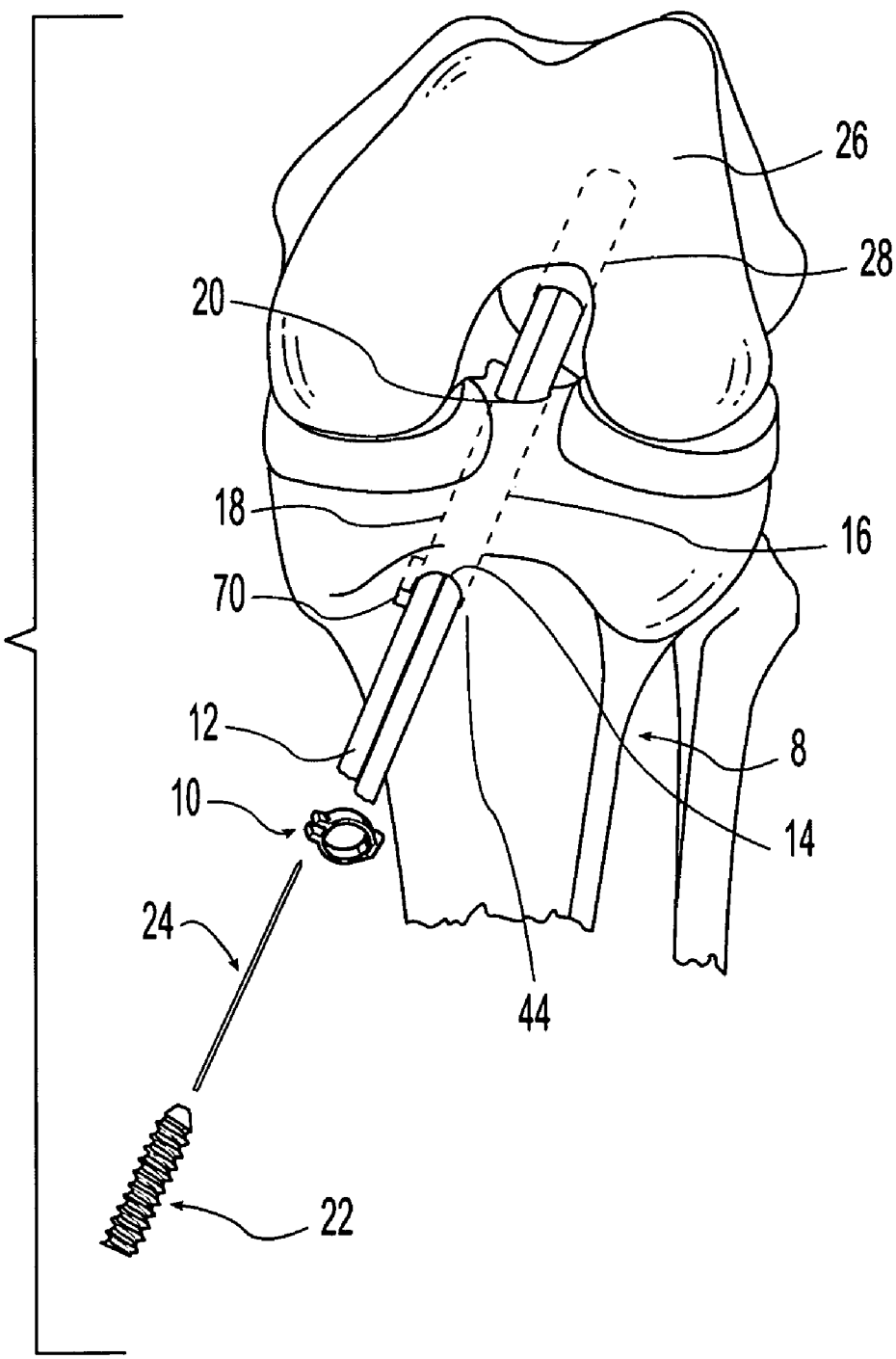
FIG. 1 is a perspective view of a human knee joint showing the implantation of an illustrative graft and graft fixation device according to the present invention.

The graft fixation system of the present invention may be used to attach any appropriate graft including, for example, supplemental and/or replacement grafts for the soft tissues associated with the skeletal system. For example, the system may be used to replace soft tissues associated with skeletal joints such as the hip, knee, shoulder, wrist, elbow, ankle, vertebral, phalangeal, temporomandibular, and other joints and locations within a body. For example, the graft fixation system may be used to attach, within a bone tunnel, grafts associated with human knee joint tissues such as the anterior cruciate ligament, the posterior cruciate ligament, the medial collateral ligament, and the lateral collateral ligament. In the illustrative embodiments, a graft fixation system is depicted for use in securing an anterior cruciate ligament graft within a tibial bone tunnel. It will be understood by those skilled in the art that this invention may be suitable for other applications as well.

Embodiments of a graft fixation system include a first member for gripping the graft and a second member for securing the first member and graft in the tunnel. The first member may include a portion for partially or fully encircling the graft. The encircling portion may include a variety of forms including open and closed and symmetric and asymmetric shapes. The encircling portion may include shapes such as cylinders, ellipses, parallelograms, "U"-shapes, "C"-shapes, "H"-shapes, and/or other suitable shapes. The encircling portion may include one or more openings for receiving the graft and/or individual strands of graft material. For example, the encircling portion may be in the form of a cylindrical ring.

The first member may also include a bone engaging portion. The bone engaging portion may include a protrusion extending outwardly from the graft encircling portion at any suitable angle. The protrusion may include a variety of forms including pins, bars, hooks, prongs, flat surfaces, and/or other suitable forms. The protrusion may include edges that are square, radiused, undercut, sharpened, and/or otherwise shaped to engage the bone. For example, the protrusion may be in the form of a sharp edged hook curving outwardly from a ring shaped encircling portion.

The first member may also include a fixation portion for engaging the second member. The fixation portion may include a variety of forms including a hole, a slot, a protrusion, a slotted protrusion, and/or other suitable form. The fixation portion may include a protrusion extending outwardly from the encircling portion at any suitable angle. For example, the fixation portion may include a slotted protrusion curving outwardly from a ring shaped encircling portion diametrically opposed to a protruding, hook shaped bone engaging portion and at an angle in the opposite direction from the bone engaging portion such that the first member appears somewhat "S"-shaped in side plan view.

The first member may be a unitary or multi-piece construction including any suitable biocompatible materials. Exemplary materials include metals, polymers, and/or other suitable materials and combinations thereof. For example, the first member may include metals including stainless steels, titanium, titanium alloys, cobalt-chromium steels, nickel-titanium alloys, and/or others. The first member may include nonresorbable polymers including polyolefins, polyesters, polyimides, polyamides, polyacrylates, poly(ketones), fluropolymers, siloxane based polymers, and/or others. The first member may include resorbable polymers including polyesters (e.g. lactide and glycolide), polyanhydrides, poly(aminoacid) polymers (e.g. tyrosine based polymers), and/or others. The first member may include other materials including nonresorbable and resorbable ceramics (e.g. hydroxyapitite, calcium sulfate) or biocompatible glasses. The first member may be constructed by machining, punching, welding, molding, sintering, and/or other suitable methods. For example, a suitable first member may be injection molded from a non-resorbable polymer such as polyetheretherketone.

The second member may include a pin, wedge, clip, bolt, screw, or other suitable member for securing the first member adjacent the bone tunnel. For example, the second member may include an interference screw able to be driven beside the first member to engage the fixation portion and press the first member into contact with the graft and bone.

The second member may be made of conventional materials such as biocompatible metals, polymers, ceramics, bioabsorbable materials and/or other suitable materials as discussed relative to the first member. For example, a suitable second member may be injection molded from a resorbable polymer.

The graft fixation system of the present invention may be used in a variety of locations in the body and it may take a variety of forms. By way of example only, the illustrative embodiments depict a two piece graft fixation system for use in securing an anterior cruciate ligament graft within a tibial bone tunnel. It will be understood by those skilled in the art that this invention may be suitable for other applications as well. FIGS. 1-7 depict an illustrative embodiment of the invention including a first member in the form of a ring 10 for encircling a portion of a graft 12 adjacent the opening 14 of a tibial 8 bone tunnel 16 having a proximal end 18 and a distal end 20. The terms "proximal" and "distal" are intended to refer to positions relative to the bone tunnel, proximal being closer to the tunnel entrance and distal being farther away. The ring 10 serves to grip the graft 12 in belt buckle fashion. The ring 10 also engages the bone in axial fixed relationship to fix the axial position of the graft 12 relative to the tibial bone tunnel 16. The graft 12 and ring 10 are secured to the tibia with a screw 22. A guidewire 24 may be used to guide the screw 22 into position. The opposite end of the graft 12 is secured to the femur 26 such as by securing it in a femoral tunnel 28 in known fashion.

Turning to FIGS. 2-5, the illustrative ring 10 includes a graft 12 encircling portion in the form of a cylindrical wall 30. The cylindrical wall 30 includes an inner surface 32 defining a lumen 34 having a lumen axis 31 and an outer surface 36. The lumen 34 is sized to receive the graft 12 and the outer surface 36 is sized to fit the bone tunnel 16. The ring 10 may be provided in a variety of sizes to fit different sizes of grafts 12 and tunnels 16.

A bone engaging portion extends radially outwardly from the cylindrical wall 30 in the form of a curved prong 38. The prong 38 also extends axially and includes a pointed or serrated tip 40 and a bone engaging underside 42. In the illustrative example, the tip 40 initially grips the tibial cortex 44 until the ring 10 is put in final position with the bone engaging underside 42 in contact with the tibial cortex 44. Optionally the tip 40 may be oriented to maintain its grip on the tibial cortex 44 at all times.

A fixation portion extends radially outwardly from the cylindrical wall 30 in the form of a broad slotted protrusion 46. The protrusion 46 is situated diametrically opposite the prong 38. The protrusion 46 also extends axially and in a direction opposite the direction of the prong 38 curvature. The protrusion 46 may include a slot 48 for engaging the optional guidewire 24. The protrusion also includes a conical or spherical depression 50 to receive the screw 22. The cylindrical wall 30 may be angled relative to the lumen axis 31 as shown in FIG. 5 to aid in implanting the ring 10 by imparting a pre-rotation to the ring 10 prior to inserting the screw 22. This pre-rotation also allows the protrusion 46 to engage a notch 70 formed in the bone tunnel prior to rotation of the ring.

In the illustrative embodiment, the second member is in the form of an interference screw 22. The screw 22 includes a proximal end 52, a distal end 54, and a thread 56 spiraling therebetween. The thread 56 includes a major diameter defined by the thread crest 58 and a minor diameter defined by the thread root 60. A bullet shaped leading taper 62 is formed adjacent the distal end 54. Optionally, the threads 56 may continue down the leading taper 62 such that the entire screw 22 is threaded. The screw 22 includes an axial through hole or cannulation 64. A tri-lobed driver recess 66 is formed at the proximal end 52 for torque transmitting engagement with a driver. The screw 22 is available in different diameters, which are chosen based on the graft 12 and tunnel 16 diameters.

FIG. 8 depicts an optional tunnel notcher 68 that may be used to create a notch 70 in the tunnel 16 entrance. The notcher 68 includes a cutter guide 72 and an elongated cutter 74. The cutter guide 72 includes a handle 76 and a cutter guide shaft 78 extending from a proximal end 80 near the handle 76 to a distal end 82 spaced from the handle 76. The cutter guide shaft 78 includes a longitudinal channel 84 opening radially outwardly along the length of the cutter guide shaft 78. The cutter 74 includes a handle 86 and a cutter shaft 87 extending from a proximal end 88 near the handle 86 to a distal end 90 spaced from the handle 86. A radially extending blade 92 extends away from the cutter shaft 87 adjacent the distal end 90. The longitudinal channel 84 of the cutter guide shaft 78 receives the cutter shaft 87 in an axial sliding manner with the blade 92 projecting out of the channel 84. The cutter guide shaft 78 is sized to fit the bone tunnel 16 and may be provided in a variety of sizes. With the cutter guide shaft 78 positioned within the tunnel 16, the cutter 74 may be slid within the channel 84 to cut a notch 70 in the tunnel 16 wall.

The method of using the invention is described with reference to FIGS. 9-11. A suitable graft 12 is procured. For example a soft tissue graft 12 may be harvested and prepared. An illustrative soft tissue graft may include semitendinosus and/or gracilis tissues. The tibial 16 and femoral 28 tunnels are drilled in the typical fashion and are sized to match the graft 12 diameter. The proximal end 18 of the inner wall of the tibial tunnel 16 is then notched 70 at a predetermined annular position using the tunnel notcher 68 if necessary to provide clearance from a protruding fixation portion of the ring 10 implant. In the illustrative example, the tunnel 16 is notched 70 to provide clearance for the broad slotted protrusion 46. In the example, the notch 70 is formed as wide as the protrusion 46 and at least as far into the tunnel 16 as necessary to allow the ring 10 to swing into the tunnel 16.

The graft 12 is then passed through the tibial 16 and femoral 28 tunnels and fixed on the femoral side in the typical fashion. The ring 10 is then passed over the graft 12 and seated such that the slotted protrusion 46 is in the notch 70 and the tip 40 of the prong 38 is on the cortical surface 44. An optional guidewire 24 may be passed into the tunnel 16 and situated within the notch 70 and slot 48. The graft 12 is tensioned and the interference screw 22 is placed over the guidewire 24 (if used). The leading end 62 of the screw 22 will engage the depression 50 in the slotted protrusion 46 to help stabilize the screw 22 and ring 10 for insertion. The screw 22 is advanced into the tunnel 16 until its proximal end 52 is flush with the tibial cortex 44. The guidewire 24 (if present) is then removed. As the screw 22 is advanced, it presses on the protrusion 46 and causes it to advance as well. The slot 48 and depression 50 of the protrusion 46 engage the thread 56 to hold the ring 10 in position. The tip 40 and/or underside 42 of the prong 38 abuts the tibial cortex 44 so that the prong 38 does not advance into the tunnel 16. As the protrusion 46 moves into the notch 70 and tunnel 16, the ring 10 rotates about the point of contact between the prong 38 and the tibial cortex 44. The ring 10 impinges the graft 12 and bends it back so that the graft 12 follows a tortuous path through the ring 10 somewhat like a belt passing through a buckle. Fixation of the graft 12 occurs primarily with the interference screw 22 as supplemented by the tortuous path created by the ring 10. The inner surface 32 of the ring 10 may be made granular by providing it with a roughened texture, radially inwardly projecting bumps, or some other feature to increase the frictional engagement between the ring 10 and the graft 12. Once the graft 12 is fixed in the tunnel 16, the portion of the graft 12 extending out of the tunnel 16 may be cut off.

FIGS. 12-15 depict a ring 100 identical to the ring 10 of FIGS. 1-11 except for the addition of optional insertion tool engagement lugs 102 projecting laterally from the prong 104. An insertion tool 110 includes a distal end 112 having a means for gripping the ring 100. In the illustrative embodiment, the means for gripping includes a pair of spaced apart projections 114 having notches 116. The ring 100 is positioned on the tool 110 with the projections straddling the prong 104 and the lugs 102 received in the notches 116 in a hinge-like arrangement. The ring 100 is able to pivot backward until the back 106 of the prong 104 contacts a stop surface 118 on the distal end 112 of the tool 110 near the projections 114 to stop the ring 100 at a known angular relationship to the tool 110. The ring 100 is free to rotate away from the stop surface 118. The tool 110 may thus be used to grip the ring 100 adjacent the prong 104 and press the prong into engagement with the tibial cortex 44. As the screw 22 is inserted, the ring 100 is permitted to pivot into the bone tunnel 16 while the tool 110 prevents the ring 100 from slipping or lifting off of the cortex 44.

Figure 16:
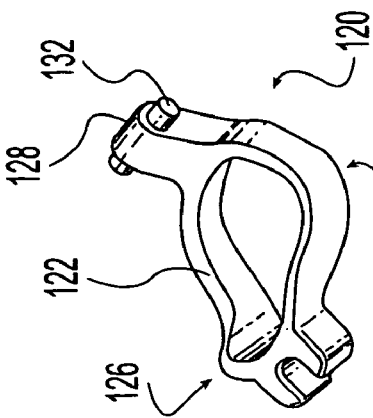
FIG. 16 is a side elevation view of the graft fixation device of FIG. 1 shown with an optional offset side wall.
Figure 17:
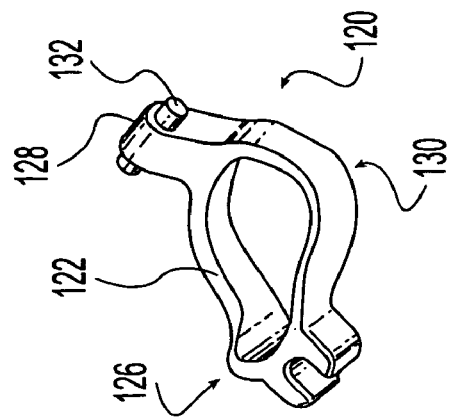
FIG. 17 is a perspective view of the graft fixation device of FIG. 1 shown with the optional offset side wall of FIG. 16.
Figure 14:
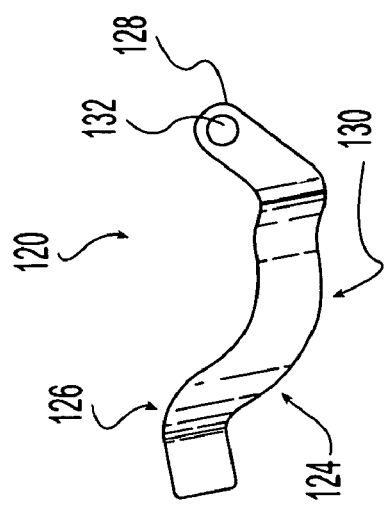
FIG. 14 is a perspective view of the graft fixation device of FIG. 1 shown with the optional insertion tool engagement lugs of FIG. 12 and being engaged with an insertion tool.
Figure 15:
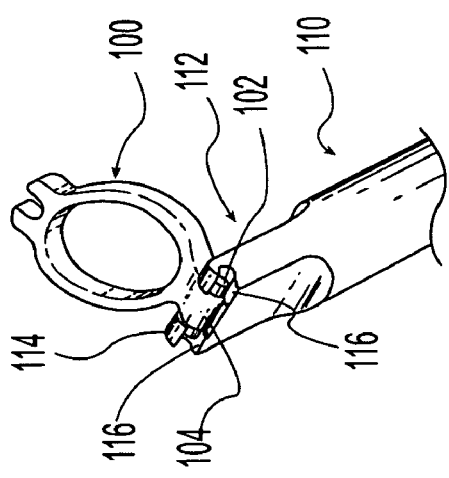
FIG. 15 is a side elevation view of the graft fixation device of FIG. 1 shown with optional insertion tool engagement lugs and being engaged with an insertion tool.
Figure 12:
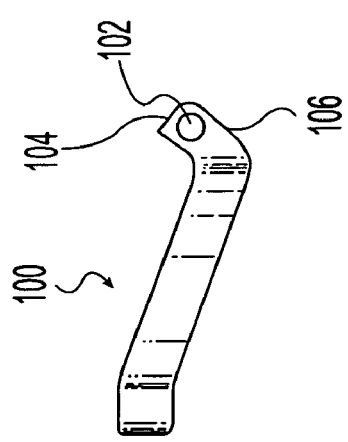
FIG. 12 is a side elevation view of the graft fixation device of FIG. 1 shown with optional insertion tool engagement lugs.
Figure 13:
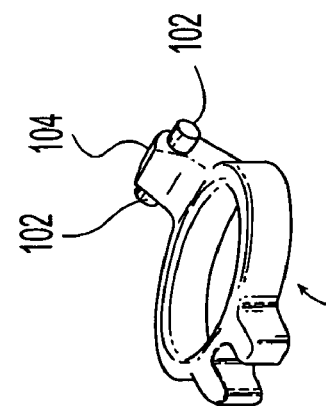
FIG. 13 is a perspective view of the graft fixation device of FIG. 1 shown with the optional insertion tool engagement lugs of FIG. 12.

FIGS. 16 and 17 depict a ring 120 identical to the ring 10 of FIGS. 1-11 except that the ring 120 of FIGS. 16 and 17 has a cylindrical side wall 122 that has an axial curve or offset 124. This offset 124 allows the ring 120 to better conform to the cylindrical bone tunnel 16 as the ring 120 rotates into the tunnel 16, and reduces the impingement of the ring 120 on the tunnel 16 wall. The belt buckle effect of the ring 120 is created by the side 126 of the ring 120 opposite the prong 128 rotating into the tunnel 16 and compressing the graft 12. Measured perpendicularly to a line connecting the prong 128 and opposite side 126, the ring 120 is widest in the middle 130 and narrowest near the prong 128 and opposite side 126. Using the same measurement direction, the tunnel is likewise widest in the middle and narrowest near the sides. Thus, as the ring 120 rotates about the prong 128, the opposite side 126 moves up and toward the center of the tunnel into contact with the graft 12. At the same time, the middle 130 of the ring moves up and away from the middle of the tunnel 16 toward the side of the tunnel 16 adjacent the prong 128. As the wider middle part 130 of the ring 120 moves into the narrower side of the tunnel 16, the ring will impinge on the tunnel 16 wall. Small amounts of impingement are permissible, since the bone will compress and permit the ring 120 to continue its rotation. However, depending on the graft 12, tunnel 16, and ring 120 geometries, it is possible that excessive impingement might occur. This impingement may either block the ring 120 from further rotation before the ring 120 develops sufficient belt buckle-like compression of the graft 12 or cause the ring 120 to rotate about the impingement point such that the prong 128 moves toward the tunnel 16. Excessive movement of the prong 128 may reduce its grip on the tibial cortex 44. Impingement may be worse in patients with less compressible, sclerotic bone. The offset 124 of the ring 120 of FIGS. 16 and 17 advances the opposite side 126 so that it compresses the graft 12 more at a given stage of rotation than non-offset rings. Thus the ring 120 is able to provide belt buckle gripping of the graft 12 with less rotation and with less likelihood of significant impingement with the tunnel 16 wall. The ring 120 of FIGS. 16 and 17 is also shown with optional insertion tool engaging lugs 132 as described relative to FIGS. 12-15.

It will be understood by those skilled in the art that numerous improvements and modifications may be made to the preferred embodiment of the invention disclosed herein without departing from the spirit and scope thereof.

What is claimed is:

1. A method for retaining a graft in a bone tunnel formed in a bone, the method comprising:
   positioning an encircling means adjacent the bone tunnel in a first position such that it at least partially encircles a portion of the graft with the graft passing generally straight through the encircling means, the encircling means comprising a lumen for receiving the graft, a prong for gripping the bone outside of the tunnel to create a center of rotation, and a fixation tab for engaging an interference screw, the step of positioning the encircling means adjacent the bone tunnel comprising placing the prong into engagement with the bone outside of the bone tunnel and placing the graft through the lumen positioning an interference screw adjacent the fixation tab; and driving the interference screw into the bone tunnel to rotate the encircling means about the center of rotation created by the prong from the first position to a second position, within the bone tunnel, in which the graft is forced into a tortuous path through the encircling means such that the encircling means grips the graft and the interference screw grips the encircling means to secure the graft and encircling means relative to the bone tunnel with the encircling means in the second position.

2. The method of claim 1 further comprising:
   forming a notch in a portion of the bone tunnel to receive the fixation tab.

3. The method of claim 2 further comprising:
   inserting a guidewire into the tunnel adjacent the notch; and
   inserting the interference screw over the guide wire to guide the interference screw.

\* \* \* \* \*